United States Patent [19]

Lee et al.

[11] 4,128,456
[45] Dec. 5, 1978

[54] SUCTION ELECTRODE FOR INTRACELLULAR POTENTIAL MEASUREMENT

[76] Inventors: Kai S. Lee, 5800 Seawall Blvd.; Norio Akaike, 300 N. Ferry Rd., Apt. 1104; Arthur M. Brown, 0915 Seawall Blvd., #216, all of Galveston, Tex. 77550

[21] Appl. No.: 840,826

[22] Filed: Oct. 11, 1977

[51] Int. Cl.² ............................................. C12K 1/10
[52] U.S. Cl. .................................. 195/127; 128/2 E; 128/2.1 E; 204/1 T; 204/195 B; 195/103.5 R
[58] Field of Search ................... 195/127; 204/195 B, 204/1 E, 1 H; 128/2 E, 2.1 E

[56] References Cited
U.S. PATENT DOCUMENTS

| | | | |
|---|---|---|---|
| 3,049,118 | 8/1962 | Arthur et al. | 128/2 E |
| 3,078,850 | 2/1963 | Schein et al. | 128/2.1 E X |
| 3,087,486 | 4/1963 | Kilpatrick | 128/2.1 E |
| 3,297,558 | 1/1967 | Hillquist | 204/1 H X |
| 4,009,078 | 2/1977 | Wilkins et al. | 195/127 X |

Primary Examiner—Alvin E. Tanenholtz
Assistant Examiner—Robert J. Warden
Attorney, Agent, or Firm—Brown & Martin

[57] ABSTRACT

An electrical sensing and stimulation electrode small enough to record intracellular activity within a single living cell. The electrode incorporates a cylindrical chamber with a finely tapered end section. The chamber is evacuated to hold the cell at its tip. Contained within the chamber are piping, circuitry, and controls to provide selected life support environment, stimulation, and continuous sensing of the iternal ionic composition of the captured cell.

8 Claims, 2 Drawing Figures

SUCTION ELECTRODE FOR INTRACELLULAR POTENTIAL MEASUREMENT

BACKGROUND OF THE INVENTION

Improved understanding of complex living cell function is important in the fields of science and medicine. Knowledge of cell activity may be gained by measuring and recording electrical potential changes occuring within a living cell. Value of research measurements are enhanced when the physical and electrical environment of the cell under study may be controlled during measurement.

Intracellular electrical measurement has application in research studies of nerve cell bodies and tissue culture cells such as smooth muscle, cardiac, and skeletal muscle. Such measurements and suitable display are also useful for demonstration in teaching laboratories.

Microelectrodes are currently used for recording activity from cell bodies of neurons. Two types of microelectrodes are generally available. One method uses a finely drawn glass tube with a sample opening of about 1 micron in diameter. The tube is filled with a conductive fluid. The liquid filled tube becomes a measuring electrode, or probe, which is inserted in the cell by use of a micromanipulator. The second method employs a fine wire with a sharpened point as the electrode. Electrical signals detected by electrodes are amplified, displayed, or recorded by equipments connected to the microelectrode.

Microelectrodes require great skill in fabrication and use. Due to their small size and light structure, difficulty is encountered in positioning the sample cell and insertion of the microelectrode. Maintenance of good electrical contact is often hard to achieve because the delicate connection to the cell is vulnerable to movement or vibration which alters electrical parameters, or breaks the circuit altogether. Further, methods of circuit connection and completion vary, and often prevent microelectrodes from providing the rapid response time sufficient to record many of the very fast events occuring in a nerve cell. Microelectrodes also do not provide for readily changing the intracellular environment of the cell membrane during measurement and study.

It is therefore desirable in research studies of nerve and tissue cells to have a compact integrated electrode which holds the sample cell firmly, has rapid time resolution, and permits changing the intracellular environment of the studied cell.

SUMMARY OF THE INVENTION

The suction electrode described herein is an easily handled and maintained laboratory research electrode, nominally measuring 4 inches in length and half inch in diameter. It permits recording of intracellular activity in single cells of few microns in diameter. Major applications of the suction electrode lie in research studies of nerve cell bodies and tissue culture cells such as smooth muscles, cardiac and skeletal muscles. It is also useful in high school and college laboratory demonstrations.

The suction electrode incorporates a tapering cylindrical perfusion chamber terminating in a smooth fire polished aperture at one end. The perfusion chamber is closed at the opposite end with a recessed rubber stopper. In operation, the perfusion chamber is evacuated to capture and holding a living cell at the small aperture. The strong vacuum developed holds the cell firmly, and is capable of removing it from a cell cluster mechanically. This vacuum holding action gives the suction electrode cell connection high vibration resistance.

A perfusion tube is mounted in the perfusion chamber stopper and runs the interior of length of the perfusion chamber. The perfusion tube carries an electrically conductive cell life support fluid of selected composition to the captured cell permitting changes in the intracellular environment. Cell life support fluid flows from the perfusion tube and then fills the perfusion chamber. The perfusion tube also mechanically supports a puncture wire for insertion into the captured cell to make electrical measurement.

A removable electrode assembly with a single input/output wire is mounted on the perfusion chamber at approximately its mid-length, and is open to the interior of the perfusion chamber via an agar salt bridge. The electrical path from the puncture wire to the electrode assembly is completed by the conductive cell life support fluid.

Interconnected components provide a source of supply for the cell life support fluid, pumping for evacuation, and a controlled reciprocation of the perfusion tube outlet and puncture wire toward and away from the captured cell.

The firm capture of the sample cell, secure electrical connections, and short conductor leads of the suction electrode facilitate low interference recordings of cell activity. Use of the agar salt bridge minimizes fluid junction potential interference at the life support fluid agar salt bridge interface. The single input/output wire enhances the response time of the system as compared to two wire sensing and stimulation circuits. As a consequence of its electrical circuitry, the suction electrode has necessary time response characteristics to permit continuous sensing of rapid changes in the ionic composition of the captured cell.

The object of this invention, therefore, is to provide a new and improved suction electrode for intracellular measurement. The suction electrode holds the sample cell firmly minimizing movement and vibration interference. It is capable of continuous rapid response for the recording of intracellular activity. The configuration of the electrode permits changing the enviornment of the cell under study by bathing it with cell life support fluid of selected ionic composition. The suction electrode employs a single sensing and stimulation wire to avoid capacitive coupling encountered in two wire methods. The electrode features ease of use and maintenance. Other objects and advantages will be apparent in the following detailed description, taken in conjunction with the accompanying drawings in which like reference numerals refer to the same parts throughout.

DETAILED DESCRIPTION OF THE DRAWINGS

Figures 1, 2:
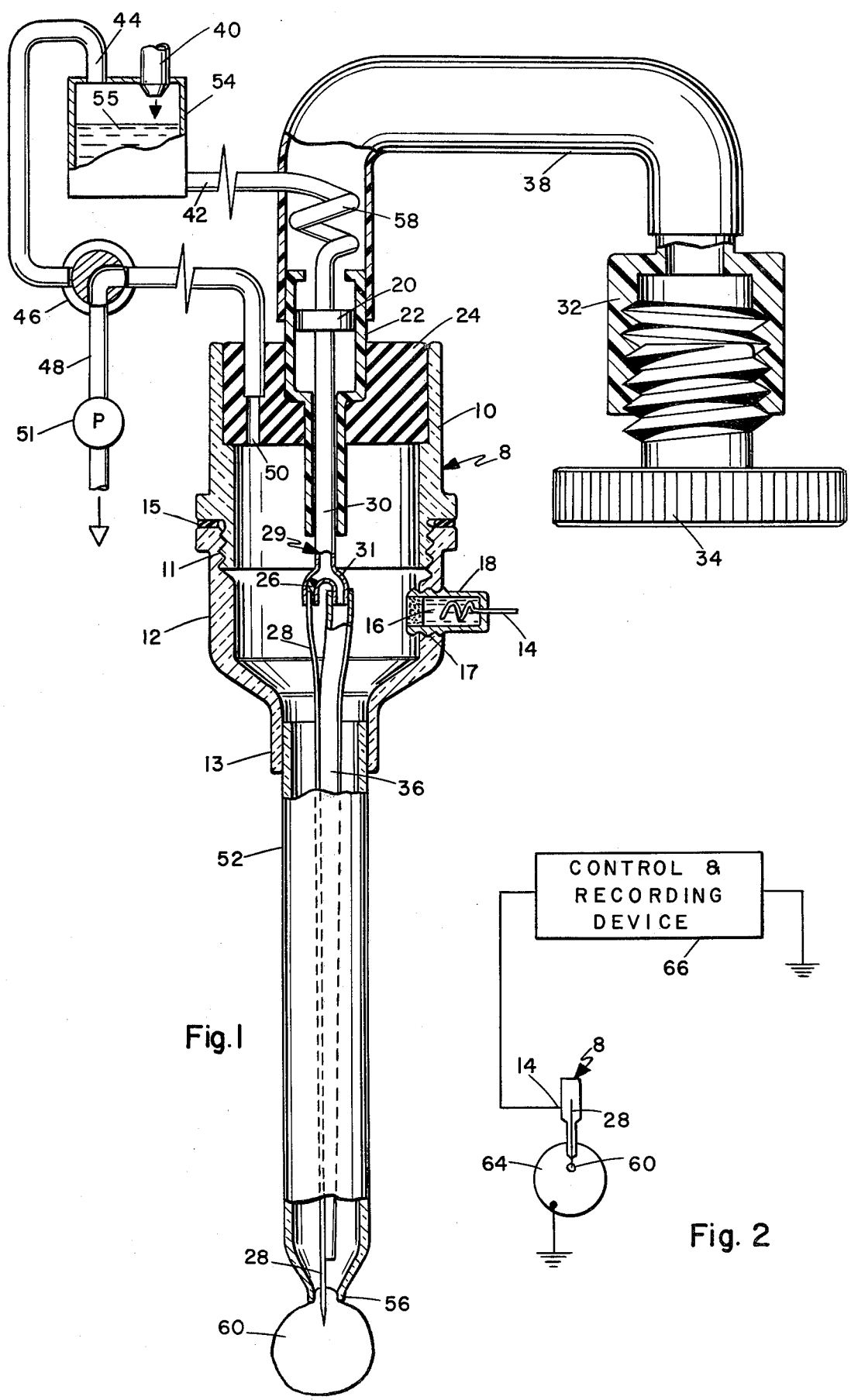
FIG. 1 is an enlarged sectional view of the suction electrode and supporting components.
FIG. 2 schematically depicts the operation of the suction electrode circuit.

For convenience of description, the basic structure of the unit is indicated as being of glass with flexible tubing joints. However, these terms should be understood as including other suitable materials, such as plastic or metal.

The suction electrode is composed of four integrated functional subassemblies namely, cell positioning, life support, sensing and stimulation, and cell penetration control. The major handling and support components of the cell positioning assembly will be described first.

The perfusion chamber 8 is the principal member of the suction electrode, formed by joining the perfusion chamber body 10 to the suction pipette adaptor 12 by use of their threaded sections 11 and an O-ring seal 15. The suction pipette 52 is sealed into the tapering opening 13 of the pipette adaptor forming a cylindrical perfusion chamber tapering to a small aperture at one end. The cell sample end 56 of the suction pipette 52 is fire polished to a smooth small opening 56 against which a captured cell 60 is held by a vacuum in the perfusion chamber 8. The perfusion chamber 8 is evacuated through opening 50 by a vacuum pump 51 attached at tubing connection 48. Valve 46 permits selection of suction on the perfusion chamber 8 or life support fluid reservoir 54 by use of connected tubing. Valve 46 is in the position shown during suction electrode operation.

The suction pipette adaptor 12 is provided with a threaded circular opening 17 to receive the electrode assembly 14, 16 and 18 at approximately its mid-length.

The upper end of the perfusion chamber 8 is closed by a holed and recessed rubber stopper 24. The stopper 24 also serves to support the perfusion tube assembly 29, of the cell life support sub-assembly.

The perfusion tube assembly 29 incorporates a permanent perfusion tube 30 to which is attached a disposable perfusion tube 36. The two sections together form piping mounted within the perfusion chamber 8, through which cell life support fluid 55 is carried to the captured cell 60. The permanent perfusion tube 30 is provided with a collar at its upper end which forms the perfusion tube piston 20. This piston moves within the control cylinder 22 with an oil tight seal to cause longitudinal motion of the perfusion tube assembly 29 within the perfusion chamber 8.

The lower end of the permanent perfusion tube 30 is provided with a "Y" connection 31, one branch of which is closed to form the puncture wire mounting 26. The disposable perfusion tube 36 is attached at the open "Y" connection forming an extension of the permanent perfusion tube 30. The cell puncture wire 28 has one end attached in the puncture wire mounting 26 and extends slightly beyond the length of the disposable perfusion tube 36. The sampling end of the puncture wire is inserted in the captured cell 60 for electrical measurement.

The perfusion tube is equipped with an expansion coil section 58 above the perfusion tube control cylinder 22 to permit longitudinal movement of the perfusion tube and puncture wire within the perfusion chamber 8. The interior of the perfusion tube expansion coil is flexibly connected to the cell life support fluid reservoir 54 at connection 42. Life support fluid 55 is placed in reservoir 54. During suction electrode operation cell life support fluid 55 is drawn through the perfusion tube assembly 29 by the vacuum maintained in the perfusion chamber, and then fills the interior of the perfusion chamber 8 after bathing the captured cell 60. The internal ionic environment of the sample cell may be altered by cell life support fluids of selected ionic composition.

The life support fluid reservoir 54 is provided with a resupply connection 40. The reservoir also has a normally closed air purge connection 44, used to remove entrained air by opening the reservoir to the vacuum pump suction 48 through the use of a vacuum control valve 46.

Cell activity sensing and stimulation are achieved through use of the sensing and stimulation electrode assembly 14, 16 and 18 mounted on the side of the perfusion chamber 8 at opening 17. The electrode assembly housing is a removable cup-shaped piece 18 screwed into the suction pipette adaptor 12. Its closed end is pierced by a single silver-silver chloride wire 14. Monitoring and stimulation equipments are connected to the suction electrode at the free end of wire 14. The remainder of the silver-silver chloride wire is embedded in an agar salt bridge 16 that fills the electrode assembly housing 18. The agar salt bridge minimizes fluid junction potential at the cell life support fluid electrode assembly interface during measurement. The sensing circuitry is completed by puncture wire 28 and the conductive cell life support fluid 55 which fills the perfusion chamber making contact with the salt agar bridge 16.

The penetration control sub-assembly incorporates the control cylinder 22, positioned in one end of the oil tube 38. The other end of the oil tube is connected to a hydrostatic micromanipulator 32. The oil tube is filled with oil. Operation of the manipulator adjustment dial 34 causes motion of the perfusion tube piston 20 within the control cylinder 22, which in turn moves the perfusion tube assembly 29 and cell puncture wire 28 toward or away from the captured cell. The perfusion tube expansion coil 58 contained within the oil tube 38 permits this motion of the perfusion tube.

FIG. 2 depicts the use of the suction electrode. Sample cell 60 within a grounded container 64 is held at the tip of the perfusion chamber 8. Puncture wire 28 is inserted into the cell. The control and recording device 66 is connected between the output electrode 14 and ground.

Having described our invention, we claim:

1. A suction electrode for intracellular measurement comprising:
   a perfusion chamber means terminating in an aperture at one end;
   means for evacuating said perfusion chamber to capture and hold a living cell at said perfusion chamber aperture;
   a perfusion tube means mounted and supported in said perfusion chamber;
   means for controlled movement of said perfusion tube means toward and away from the captured cell;
   cell sensing means movable with said perfusion tube for passage through said perfusion chamber aperture, penetration of the captured cell and sensing cell internal electrical activity;
   means for delivering an electrically conductive cell life support fluid to the captured cell through said perfusion tube;
   means for conduction of sensed intracellular electrical signals from the interior of said perfusion chamber to external equipment.

2. A suction electrode for intracellular measurement according to claim 1, wherein said perfusion chamber means further comprises:
   a holed and recessed stopper means for closing the second end of said perfusion chamber;
   a perfusion chamber incorporating a cylindrical chamber tapering to an aperture at one end.

3. A suction electrode for intracellular measurement according to claim 2, wherein:

said perfusion tube means is mounted in said perfusion chamber holed and recessed stopper means and runs the interior length of said perfusion chamber.

4. A suction electrode according to claim 3, wherein said perfusion tube means further comprises:
- a perfusion tube cylinder mounted in said holed and recessed stopper means;
- a permanent perfusion tube, fitted with a collar at its upper end, said collar being mounted in said perfusion tube cylinder forming a piston;
- said permanent perfusion tube provided with a "Y" connection at the lower end with one of the openings closed off;
- a disposable perfusion tube fitted in the open "Y" connection of said permanent perfusion tube and extending to the tapered opening of said perfusion chamber;
- a perfusion tube expansion coil formed by a toroidal section of tubing located above said perfusion tube collar;
- a non-integral life support fluid reservoir to which said expansion coil is connected;
- said life support fluid reservoir provided with filling and air purge connections.

5. A suction electrode according to claim 4, wherein said cell sensing means further comprises:
- an electrode assembly means mounted in the side of said perfusion chamber for electrically connecting the interior of said perfusion chamber to external equipment;
- a puncture wire, one end of which is attached at said closed off "Y" connection of said permanent perfusion tube, and extending the length of said disposable perfusion tube;
- an electrically conductive cell life support means for filling said perfusion tube and perfusion chamber.

6. A suction electrode according to claim 2, wherein said perfusion chamber means further comprises:
- a cylindrical perfusion chamber body with exterior threads at one end, and with the other end closed by said stopper means;
- a suction pipette adaptor, a cylindrical section tapered at one end and provided with internal threads at the opposite end for connection to said perfusion chamber body;
- said suction pipette adaptor containing a circular threaded opening at approximately mid-length;
- a suction pipette fitted into the tapered end of said suction pipette adaptor at one end and with the free end fire polished to a smooth small aperture against which the captured cell is held.

7. A suction electrode according to claim 6, wherein said electrode assembly comprises:
- a cup shaped electrode housing attached in said threaded circular opening of said suction pipette adaptor;
- an agar salt gelatin filling the interior of said assembly housing;
- a single silver-silver chloride wire embedded in said agar salt gelatin and with one end penetrating the base of said electrode housing.

8. A suction electrode according to claim 1, wherein said means for control movement of said perfusion tube comprises:
- a flexible oil tube, one end of which encloses said perfusion tube expansion coil and which terminates in said perfusion tube cylinder;
- a hydrostatic micromanipulator means for movement of the permanent perfusion tube collar, and attached at the opposite end of said flexible oil tube;
- an oil fluid means for filling said oil tube and serving as a hydraulic control medium.

* * * * *